United States Patent [19]

Van Kruchten

[11] Patent Number: 5,874,653
[45] Date of Patent: Feb. 23, 1999

[54] PROCESS FOR THE PREPARATION OF ALKYLENE GLYCOLS

[75] Inventor: Eugene Marie Godfried Andre Van Kruchten, Amsterdam, Netherlands

[73] Assignee: Shell Oil Company, Houston, Tex.

[21] Appl. No.: 756,102

[22] Filed: Nov. 25, 1996

[30] Foreign Application Priority Data

Nov. 23, 1995 [EP] European Pat. Off. ............. 95203226

[51] Int. Cl.$^6$ .................................................. C07C 27/00
[52] U.S. Cl. ............................................................ 568/867
[58] Field of Search .................................. 568/852, 857, 568/867; 525/474; 521/30

[56] References Cited

U.S. PATENT DOCUMENTS

| | | | |
|---|---|---|---|
| 4,410,669 | 10/1983 | Panster et al. | 525/474 |
| 5,130,369 | 7/1992 | Hughes et al. | 524/846 |
| 5,286,885 | 2/1994 | Goetz et al. | 549/531 |

FOREIGN PATENT DOCUMENTS

| | | | |
|---|---|---|---|
| 0065643 | 4/1982 | European Pat. Off. | C08G 77/54 |
| 0156449 | 3/1985 | European Pat. Off. | C07C 29/10 |
| 0160330 | 3/1985 | European Pat. Off. | C07C 31/20 |
| 57139026 | 2/1981 | Japan | B01J 31/08 |
| 2001901 | 10/1993 | Russian Federation | C07C 29/10 |
| 95/20559 | 1/1995 | WIPO | C07C 29/10 |

*Primary Examiner*—Michael L. Shippen
*Attorney, Agent, or Firm*—Dennis V. Carmen

[57] ABSTRACT

A process is disclosed for preparing an alkylene glycol by reacting an alkylene oxide with water in the presence of a catalyst comprising a polymeric organosiloxane ammonium salt having a silica-like skeleton and comprising units of the general formula (I)

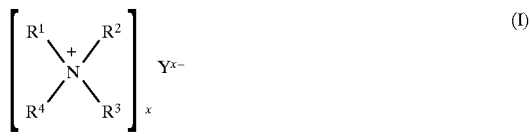

wherein $R^1$ to $R^4$, Y and x are as specified in claim 1. Preferred are the catalysts wherein the anion Y is selected from the group of carboxylates having from 1–20 carbon atoms, hydrogen carbonate, hydrogen sulphite, hydrogen phosphate and metalate. These catalysts exhibit an enhanced selectivity stability.

10 Claims, No Drawings

PROCESS FOR THE PREPARATION OF ALKYLENE GLYCOLS

FIELD OF THE INVENTION

The invention relates to a process for the preparation of alkylene glycols by reaction of an alkylene oxide with water in the presence of a catalyst.

BACKGROUND OF THE ART

Alkylene glycols, in particular monoalkylene glycols, are of established commercial interest. For example, monoalkylene glycols are being used in anti-freeze compositions, as solvents and as base materials in the production of polyethylene terephthalates e.g. for fibres or bottles.

The production of alkylene glycols by hydrolysis of alkylene oxides is known. It is performed either by liquid phase hydration with an excess amount of water, e.g. of 20 to 25 moles of water per mole of alkylene oxide, or by hydration in a heterogeneous system. The reaction is deemed to be a nucleophilic substitution reaction, whereby opening of the alkylene oxide ring occurs, water acting as the nucleophile. Because the primarily formed monoalkylene glycol likewise acts as nucleophile, as a rule a mixture of monoalkylene glycol, dialkylene glycol and higher alkylene glycols is formed. In order to increase the selectivity to monoalkylene glycols, it is necessary to suppress the secondary reaction between the primary product and alkylene oxide, which competes with the hydrolysis of alkylene oxide.

One effective means for suppressing the secondary reaction is to increase the relative amount of water present in the reaction mixture. Although the selectivity with respect to the monoalkylene glycol is thus improved, a problem is created in that for the recovery of the monoalkylene glycol from the reaction mixture large amounts of water have to be removed, which in turn involves large energy expenditure and is economically unattractive.

Considerable efforts have been made to find alternatives for increasing the selectivity of the process with respect to the monoalkylene glycols, without having to use a large excess of water. Usually, these efforts have focused on the selection of more active hydration catalysts and there are many publications, in which results obtained with various types of catalysts are disclosed.

Both acid and alkaline hydration catalysts have been investigated, whereby it would appear that the use of acid catalysts enhances the reaction rate without significantly affecting the selectivity, whereas by using alkaline catalysts generally lower selectivities with respect to the monoalkylene glycol are obtained.

High conversions, good selectivity and a low water/alkylene oxide ratio can be obtained with the process, disclosed in EP-A-156.449. According to this document, the hydrolysis of alkylene oxides is carried out in the presence of a selectivity-enhancing metalate anion-containing material, preferably a solid having electropositive complexing sites having affinity for the metalate anions. The said solid is preferably an anion exchange resin, the metalate anions are specified as molybdate, tungstate, metavanadate, hydrogenpyrovanadate and pyrovanadate anions. A complication of this process is that the alkylene glycol-containing product stream also comprises a substantial amount of metalate anions, displaced from the electropositive complexing sites of the solid metalate anion containing material. In order to reduce the amount of metalate anions in the alkylene glycol product stream, this stream is contacted with a solid having electropositive complexing sites associated with anions which are replaceable by the said metalate anions.

It has been proposed to simplify the product recovery procedure by using water-insoluble vanadate and molybdate salts. However, with these metalate anion salts the obtained selectivities are significantly lower than with the water-soluble metalates.

In JP-A-57-139026 there is disclosed a method for reacting alkylene oxide with water in the presence of a halogen type anion exchange resin and in the co-presence of carbon dioxide.

In RU-C-2001901 it is pointed out that the former disclosure has the disadvantage of the formation of carbonates in the reaction mixture which are difficult to separate from the glycols on account of the closeness of their boiling points. This patent publication discloses as its invention the performance of the alkylene oxide hydrating reaction in one or a sequence of 'extrusion reactor(s)' (continuous reaction), in the presence of 'anionite' (anion exchange resin of the quaternary ammonium type) in bicarbonate form and carbon dioxide. The essential difference with the former, Japanese, patent publication appears to be the use of the bicarbonate form of the anion exchanger instead of the halogen form thereof. And yet, the Russian patent does not dispense with the addition of carbon dioxide to the feed.

According to WO 95/20559, the presence of carbon dioxide in the feed is detrimental to the catalytic effect of bicarbonate-exchanged resins of the quaternary ammonium type. In this document there is disclosed a process for the preparation of alkylene glycols wherein an alkylene oxide is reacted with water in the presence of a catalyst composition comprising a solid material having one or more electropositive sites, which are coordinated with one or more anions other than metalate or halogen anions, with the proviso that when the solid material is an anionic exchange resin of the quaternary ammonium type and the anion is bicarbonate the process is performed in the substantial absence of carbon dioxide.

A drawback shared by the conventional anionic exchange resins which are based on purely organic polymers is their limited tolerance to heat. In practicing the process of alkylene oxide hydrolysis according to WO 95/20559 with catalyst compositions based on conventional purely organic quaternary ammonium ion exchangers it has been unexpectedly found, that under severe reaction conditions (high temperature and/or long service) the selectivity of the conventional resin-based catalysts tends to deteriorate strongly while their activity is even enhanced.

Anion exchanging polymeric organosiloxane ammonium salts have been known for some time, but their use as carriers in the instant process has never been contemplated before.

In EP-B 0 065 643 (corresponding to U.S. Pat. No. 4,410,669) polymeric ammonium compounds with a silica type backbone are disclosed, comprising units of the general formula (III)

in which $R^1$ and $R^2$ represent a group of the general formula (II)

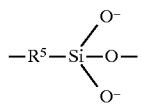

in which $R^5$ is linear or branched alkylene having 1 to 10 C atoms, cycloalkylene having 5 to 8 C atoms,

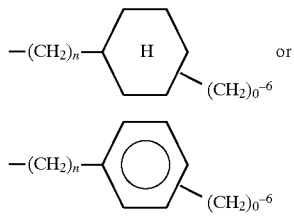

in which n is a number from 1 to 6 and indicates the number of nitrogen-terminated methylene groups, and $R^1$ and $R^2$ can be the same or different, and the free valencies of the oxygen atoms are saturated either by silicon atoms of further groups of the formula (II) and/or by crosslinking bridge members of the formula:

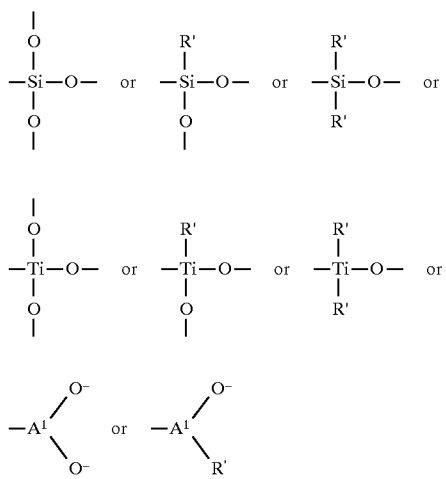

in which
R' is methyl or ethyl and the ratio of the silicon atoms in (II) to the bridge atoms silicon, titanium and aluminum is 1:0 to 1:10, $R^3$ and $R^4$ can have the same scope of meaning as $R^1$ and $R^2$ or represent hydrogen, a linear or branched alkyl containing 1 to 20 C atoms, cycloalkyl containing 5 to 8 C atoms or the benzyl group and $R^3$ and $R^4$ can be identical or different and be identical or different to $R^1$ and/or $R^2$ X represents an inorganic or organic, 1- to 3-valent anion of an inorganic or organic protonic acid which forms stable salts with amine bases and x is a number from 1 to 3.

In EP-B 0 065 643 it is also indicated in general terms, that the polymeric organosiloxane ammonium salts are useful as ion exchangers, catalytic carriers or active substance carriers.

In EP-B 0 327 796 (corresponding to U.S. Pat. No. 5,130,396) a method is disclosed for preparing the above organosiloxane amine compounds in spherical form.

In EP-A 0 491 144 (corresponding to U.S. Pat. No. 5,286,885) there are disclosed polymeric organosiloxane amine compounds, having units as in the formula (III) above with the proviso that X is an anion of a monooxo acid, an isopolyoxo acid or a heteropolyoxo acid of the elements vanadium, niobium, tantalum, molybdenum to tungsten. The use of these compounds as catalysts in oxidation reactions whereby peroxo compounds are involved is also disclosed.

SUMMARY OF THE INVENTION

The present invention now relates to a process for preparing an alkylene glycol by reacting an alkylene oxide with water in the presence of a catalyst comprising a polymeric organosiloxane ammonium salt having a silica-like skeleton and including units of formula (I)

wherein the definitions are as given above for formula (III) with the proviso that the anion Y is not a halogen. Preferably Y is one or more of the anions selected from the group of carboxylates having from 1–20 carbon atoms, hydrogen carbonate, hydrogen sulphite, hydrogen phosphate and metalate.

DETAILED DESCRIPTION OF THE INVENTION

More preferably in the catalytic polymers according to formula (I), the anion Y is selected from the group of hydrogen carbonate (bicarbonate), hydrogen sulphite (bisulphite), formate, vanadate, molybdate, tungstenate, niobate, tantalate, perrhenate or mixtures thereof. Most preferred are one or more anions selected from the group of hydrogen carbonate, hydrogen sulphite, formate and molybdate.

The catalytic polymers according to formula (I) can be prepared by processes as described for the polymeric organosiloxane ammonium compounds of formula (III) in the above identified EP-B 0 065 643 and, preferably, EP-B 0 327 796. Alternatively they can be prepared from one of the latter compounds the anion of which is within the definition of X which is available commercially, in particular one in which the anion X is a halide, such as chloride—by ion exchanging thereof with a protonic acid the anion of which is according to the above definition of Y.

Preferably in the catalytic polymers according to formula (I), $R^3$ has the same definition as $R^1$ and $R^2$, and $R^4$ is not hydrogen. More preferably, $R^1$, $R^2$ and $R^3$ are identical to each other and $R^4$ is methyl.

The most preferred catalytic polymers according to the present invention comprise units which are chosen from the formulae $[(H_3C)N(CH_2CH_2CH_2SiO_{3/2})_3]^+ \ Y^-$;

$[N(CH_2CH_2CH_2SiO_{3/2})_4]^+ \ Y^-$; or $[HN(CH_2CH_2CH_2SiO_{3/2})_3]^+ \ Y^-$ wherein the anion Y is as defined above.

The physical form in which the catalytic polymers according to formula (I) are to be used is preferably the spherical form, as described in the above identified EP-B 0 327 796. They have a diameter of 0.01–3.0 mm, a specific surface area (B.E.T.) of up to 1000 m²/g, a specific pore volume of 0–5 ml/g, a bulk density of 50–1000 g/l and a dry substance weight of 50–750 g/l. Spheres within these specifications but in the chloride form, having an effective capacity of 0.6 to 1.2 eq/l, are presently marketed by DEGUSSA under the tradename DELOXAN AMP I. They can be converted to catalysts according to the present invention by ion exchange.

The alkylene oxides, used as starting material in the process of the invention, have their conventional definition, i.e. they are compounds having a vicinal oxide (epoxy) group in their molecules.

Particularly suitable are alkylene oxides of the general formula wherein $R^6$ to $R^9$ independently represent a hydrogen atom or an, optionally substituted, alkyl group having from 1 to 6 carbon atoms. Any alkyl group, represented by $R^6$, $R^7$, $R^8$ and/or $R^9$, preferably

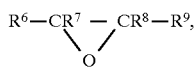

has from 1 to 3 carbon atoms. As substituents, inactive moieties, such as hydroxy groups may be present. Preferably, $R^6$, $R^7$, and $R^8$ represent hydrogen atoms and $R^9$ represents a non-substituted $C_1$–$C_3$-alkyl group and, more preferably, $R^6$, $R^7$, $R^8$ and $R^9$ all represent hydrogen atoms.

Examples of suitable alkylene oxides therefore include ethylene oxide, propylene oxide, 1,2-epoxybutane, 2,3-epoxybutane and glycidol. Ethylene oxide and propylene oxide are of particular commercial importance.

As mentioned above, it is advantageous to perform the hydrolysis of the alkylene oxides, without using excessive amounts of water. In the process according to the present invention, amounts of water in the range of 1 to 15 moles per mole of alkylene oxide are quite suitable, amounts in the range of 1 to 6 on the same basis being preferred. In the process of the invention high selectivities with respect to the monoalkylene glycol are often already achieved, when only 4 or 5 moles of water per mole of alkylene oxide are supplied.

The process of the invention may be carried out in batch operation. However, in particular for large scale embodiments it is preferred to operate the process continuously.

In order to obtain adequate time-yield values, it is recommended to perform the process under elevated temperature and pressure conditions.

Suitable reaction temperatures are generally in the range from 80° to 200° C., whereby temperatures in the range from 90° to 150° C. are preferred. The reaction pressure is usually selected in the range of 200 to 3000, preferably 200 to 2000 kPa. For batch operations of the process, the selected reaction pressure is advantageously obtained by pressurizing with an inert gas, such as nitrogen. If desired, mixtures of gases may be used, for example a mixture of carbon dioxide and nitrogen is in certain instances advantageous.

The following examples will illustrate the invention.

EXAMPLES

In these examples, the performance of catalysts based on a conventional strongly basic ion exchange resin of the quaternary ammonium type was compared to that of catalysts based on a strongly basic ion exchange resin of the polysiloxane type with quaternary ammonium groups according to the present invention. Of primary interest is the comparison of the catalyst performance after exposing the catalyst to a heat treatment.

I. The Anion Exchange Resins

The conventional (matrix: polystyrene crosslinked with divinylbenzene) strongly basic ion exchange resin of the quaternary ammonium type used in these examples for comparison was LEWATIT M500WS (ex-Bayer, chloride form), comprising matrix units of the formula

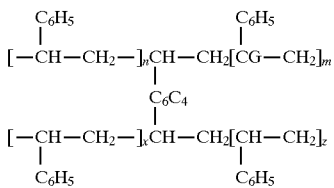

with active groups of the quaternary ammonium type

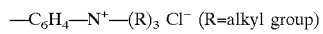

and having the following specifications:
Bead size 0.4–1.25 mm; Effective size 0.53 mm; Density 1.09 g/ml; water content 40–45% and effective capacity 1.4–1.5 eq/l of the resin.

The strongly basic ion exchange resin of the polysiloxane type with quaternary ammonium groups used was DELOXAN AMP I-1 (ex-Degussa, chloride form), comprising units of the formula

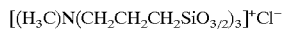

and having the following specifications:
Specific surface area (B.E.T.)<100 m²/g; Pore volume<0.2 ml/g; Bulk density (amount of dry substance in g per l of wet material) 500–550 g/l; true density 1.45 g/ml; water content 25–30% and effective capacity 1.0–1.2 eq/l of the resin.

II. Catalysts Preparation

Both types of ion exchange resins were converted to catalysts by exchanging their chloride anions to hydrocarbonate (bicarbonate), formate and molybdate anions using the following procedures.

Catalyst A (Bicarbonate based on LEWATIT M 500 WS)
150 ml (69.12 g) of wet resin was slurried in a water filled glass tube (60×2.5 cm)
the resin was washed with 375 ml of methanol for 1 h (LHSV: 2.5 l/l.h)
the resin was dried with a stream of nitrogen for 1.5 hrs
chloride was exchanged for bicarbonate by treatment with an aqueous sodium bicarbonate solution (192 g of $NaHCO_3$ in 2500 g of water; 10 molar excess) for appr. 5 hrs (LHSV: 4 l/l.h)
the exchanged resin was washed with 1200 ml of water for 2 h (LHSV: 4 l/l.h), to provide Catalyst A in which 99.9% of the original chlorine anions were replaced by bicarbonate:
chloride content of untreated dried resin: 12.35% wt
chloride content of exchanged dried resin: 70 ppm Catalyst B (bicarbonate based on DELOXAN AMP I-1)
The DELOXAN was treated exactly as described above for the LEWATIT resin, to provide Catalyst B in which 98.8% of the original chlorine anions were replaced by bicarbonate:
chloride content of untreated dried resin: 9.44% wt
chloride content of exchanged dried resin: 1125 ppm Catalyst C (formate based on DELOXAN AMP I-1)
150 ml (120 g) of wet resin was slurried in a water filled glass tube (60×2.5 cm)
the resin was washed with 375 ml of methanol for 1 h (LHSV: 2.5 l/l.h)

- the resin was dried with a stream of nitrogen for 1.5 hrs
- chloride was exchanged by formate by treatment with an aqueous sodium formate solution (156 g of HCOONa in 2500 g of water; 10 molar excess) for appr. 5 hrs (LHSV: 4 l/l.h)
- the exchanged resin was washed with 1200 ml of water for 2 h (LHSV: 4 l/l.h), to provide Catalyst C in which 95.1% of the original chlorine anions were replaced by formate:
- chloride content of untreated dried resin: 9.44% wt
- chloride content of exchanged dried resin: 4637 ppm Catalyst D (hydroxide based on DELOXAN AMP I-1)

DELOXAN AMP I-1 was converted to the OH-form by washing with a stoichiometric amount of sodium hydroxide.

Catalyst E (molybdate based on DELOXAN AMP I-1)

103 g (150 ml) of the DELOXAN resin was treated exactly as described above for the Lewatit resin, to provide catalyst E in which 99.8% of the original chlorine anions were replaced by bicarbonate:
- chloride content of untreated dried resin: 9.44% wt
- chloride content of exchanged dried resin: 89 ppm

III. Heat Treatment

A sample of each of the catalysts A to E (approximately 100 ml of wet catalyst) was suspended in approximately 120 ml of an 1/1 (v/v) mixture water/monoethylene glycol and kept at 100° C. for 600 hrs under an atmosphere of nitrogen.

IV. Batch Experiments: Conversion of EO to MEG

A 550 ml autoclave was filled with the catalyst (13 g of air-dried catalyst), water (90 g; 5 mol) and EO (44 g; 1 mol) and heated over 15 min to 60° C. at 1100 pKa gas pressure. The gas added was pure nitrogen. The reaction mixture was maintained under continuous stirring for the given time at that temperature. The results in terms of EO conversion and selectivity to MEG are compiled in the Table below.

TABLE

| Catalyst | Runtime (h) | EO conversion (% mol) | MEG selectivity (% mol) |
|---|---|---|---|
| A | 6.2 | 72.2 | 95.3 |
| A* | 1.0 | 76.6 | 40.0 |
| A | 7.0 | 99.7 | 33.2 |
| B | 6.3 | 64.8 | 95.0 |
| B* | 7.0 | 57.9 | 94.5 |
| C | 5.6 | 42.9 | 93.8 |
| C | 6.8 | 49.7 | 93.1 |
| C* | 5.9 | 47.2 | 93.7 |
| D | 4.0 | 37.5 | 95.4 |
| D* | 5.3 | 38.4 | 95.6 |
| E | 5.8 | 46.0 | 93.6 |
| E* | 5.5 | 32.1 | 93.1 |

*catalyst having been kept in 1/1 water/MEG mixture under nitrogen at 100° C. for 600 hrs.

From these results it appears, that the performance in terms of selectivity to MEG of the catalysts according to the invention B, C, D and E was not affected by the previously undergone severe heat treatment. By contrast, in the comparative catalyst A the same heat treatment resulted in considerable loss of selectivity, albeit that the reactivity (EO conversion) increased. Note that high selectivity is much more important in the subject process than is high reactivity.

I claim:

1. A process for preparing an alkylene glycol by reacting an alkylene oxide with water in the presence of a catalyst comprising a polymeric organosiloxane ammonium salt having a silica-like skeleton and comprising units of the general formula (I)

in which $R^1$ and $R^2$ represent a group of the general formula (II)

in which $R^5$ is linear or branched alkylene having 1 to 10 C atoms, cycloalkylene having 5 to 8 C atoms,

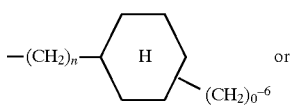

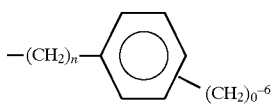

in which n is a number from 1 to 6 and indicates the number of nitrogen-terminated methylene groups, and $R^1$ and $R^2$ can be the same or different, and the free valencies of the oxygen atoms are saturated either by silicon atoms of further groups of the formula (II) and/or by crosslinking bridge members of the formula:

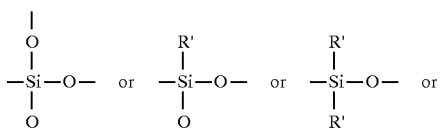

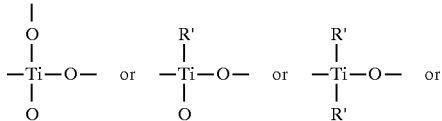

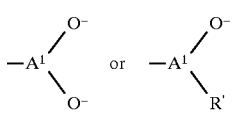

in which
  R' is methyl or ethyl and the ratio of the silicon atoms in (II) to the bridge atoms silicon, titanium and aluminum is 1:0 to 1:10,
  $R^3$ and $R^4$ can have the same scope of meaning as $R^1$ and $R^2$ or represent hydrogen, a linear or branched alkyl containing 1 to 20 C atoms, cycloalkyl containing 5 to 8 C atoms or the benzyl group and $R^3$ and $R^4$ can be identical or different and be identical or different to $R^1$ and/or $R^2$,
  Y represents an inorganic or organic, 1- to 3-valent anion, excluding halogens, and metalates of an inorganic or organic protonic acid which forms stable salts with amine bases and x is a number from 1 to 3.

2. A process according to claim 1, wherein Y is one or more of the anions selected from the group consisting of carboxylates having from 1–20 carbon atoms, hydrogen carbonate, hydrogen sulphite, and hydrogen phosphate.

3. A process according to claim 2, wherein Y is one or more of the anions selected from the group consisting of hydrogen carbonate (bicarbonate), hydrogen sulphite (bisulphite), formate, and mixtures thereof.

4. A process according to claim 3, wherein Y is one or more anions selected from the group consisting of hydrogen carbonate, hydrogen sulphite, and formate.

5. A process according to claim 1, wherein $R^3$ has the same definition as $R^1$ and $R^2$, and $R^4$ is not hydrogen.

6. A process according to claim 5, wherein $R^1$, $R^2$ and $R^3$ are identical to each other and $R^4$ is methyl.

7. A process according to claim 6, wherein the catalyst comprises units chosen from the formulae $[(H_3C)N(CH_2CH_2CH_2SiO_{3/2})_3]^+ \ Y^-$;

$[N(CH_2CH_2CH_2SiO_{3/2})_4]^+ \ Y^-$; or $[HN(CH_2CH_2CH_2SiO_{3/2})_3]^+ \ Y^-$.

8. A process according to any one of claims 1, wherein the catalyst is in the form of spherical particles, having a diameter of 0.01–3.0 mm, a specific surface area (B.E.T.) of up to 1000 $m^2/g$, a specific pore volume of 0–5 ml/g, a bulk density of 50–1000 g/l and a dry substance weight of 50–750 g/l.

9. A process according to claim 1, characterized in that the alkylene oxide is chosen from the group of ethylene oxide and propylene oxide.

10. A process according to claim 8, characterized in that the molar ratio between water and alkylene oxide is in the range of 1:1 to 15:1, the reaction temperature is in the range of 80°–200° C. and the pressure is in the range of 200–3000 kPa.

* * * * *